US012616803B2

(12) United States Patent
Lanham

(10) Patent No.: US 12,616,803 B2
(45) Date of Patent: May 5, 2026

(54) APPARATUS FOR DISPENSING INHALANT MEDICAMENT

(71) Applicant: Metopi LLC, Alexandria, VA (US)

(72) Inventor: Miles Lanham, Alexandria, VA (US)

(73) Assignee: Metopi Pharmaceuticals, Inc., Alexandria, VA (US)

( * ) Notice: Subject to any disclaimer, the term of this patent is extended or adjusted under 35 U.S.C. 154(b) by 0 days.

(21) Appl. No.: 19/232,721

(22) Filed: Jun. 9, 2025

(65) Prior Publication Data

US 2025/0375581 A1 Dec. 11, 2025

Related U.S. Application Data

(60) Provisional application No. 63/793,605, filed on Apr. 23, 2025, provisional application No. 63/793,055, filed on Apr. 23, 2025, provisional application No. 63/684,512, filed on Aug. 19, 2024, provisional application No. 63/661,580, filed on Jun. 19, 2024, provisional application No. 63/657,151, filed on Jun. 7, 2024.

(51) Int. Cl.
*A61M 15/00* (2006.01)

(52) U.S. Cl.
CPC .... *A61M 15/0025* (2014.02); *A61M 15/0071* (2014.02); *A61M 15/009* (2013.01); *A61M 2202/064* (2013.01)

(58) Field of Classification Search
CPC ........... A61M 15/0021–0026; A61M 15/0071; A61M 15/009; A61M 2202/064
See application file for complete search history.

(56) References Cited

U.S. PATENT DOCUMENTS

| | | | |
|---|---|---|---|
| 4,130,116 A | 12/1978 | Cavazza | |
| 4,817,822 A * | 4/1989 | Rand ................... | A61M 15/009 128/200.14 |
| 2007/0119450 A1 | 5/2007 | Wharton et al. | |
| 2008/0251551 A1* | 10/2008 | Huber ................. | A61M 15/009 128/200.23 |
| 2010/0083963 A1* | 4/2010 | Wharton ............. | A61M 15/009 128/203.15 |
| 2016/0022933 A1 | 1/2016 | Ciancone et al. | |
| 2016/0279355 A1 | 9/2016 | Malhotra et al. | |
| 2016/0375207 A1 | 12/2016 | Bhide et al. | |

FOREIGN PATENT DOCUMENTS

| | | | | |
|---|---|---|---|---|
| GB | 2074454 A | * | 11/1981 | ........ A61M 15/0023 |
| WO | 2008110584 A2 | | 9/2008 | |

OTHER PUBLICATIONS

Application No. PCT/US2025/032928, International Search Report and Written Opinion dated Sep. 2, 2025.

* cited by examiner

*Primary Examiner* — Elliot S Ruddie

(74) *Attorney, Agent, or Firm* — Woods Rogers Vandeventer Black PLC; Nathan A. Evans

(57) ABSTRACT

An inhaler apparatus for dispensing an inhalant medicament.

16 Claims, 13 Drawing Sheets

APPARATUS FOR DISPENSING INHALANT MEDICAMENT

CROSS-REFERENCE TO RELATED APPLICATIONS

The present application relies on the disclosures of and claims priority to and the benefit of the filing dates of U.S. Provisional Application Nos. 63/657,151, filed Jun. 7, 2024, 63/661,580, filed Jun. 19, 2024, 63/684,512, filed Aug. 19, 2024, 63/793,055, filed Apr. 23, 2025, and 63/793,605, filed Apr. 23, 2025. The disclosures of those references are hereby incorporated by reference herein in their entirety.

FIELD OF THE INVENTION

The present disclosure is directed to the field of portable apparatus for dispensing inhalant medicaments, which are configured to improve safety, portability, convenience, and effectiveness, of using the inhalant medicament, such as, by of example only, an asthma medicament.

BACKGROUND

Asthma and other respiratory conditions are commonly managed with inhalant medications delivered through portable inhalers. Existing inhalers, such as metered-dose inhalers (MDIs), dry powder inhalers (DPIs), and soft mist inhalers, have become standard devices for administering medication quickly and efficiently. However, these conventional inhalers are often associated with several limitations that can impact their effectiveness, ease of use, and safety.

One common issue with current inhalers is their susceptibility to contamination and medication degradation due to exposure to environmental contaminants such as dust, moisture, and dirt. Many inhalers lack effective protective features, requiring users to handle the device carefully to maintain medication integrity. Additionally, the mouthpieces in traditional inhalers are often exposed when not in use, increasing the risk of cross-contamination and accidental inhalation of foreign particles. Other common issues include susceptibility to forgetting to bring an inhaler when on the go, as well as inconvenience or uncomfortably carrying traditional inhalers.

Another significant challenge is the difficulty some users face in correctly positioning and operating their inhaler devices, which can lead to improper delivery of medication and suboptimal therapeutic outcomes. For example, difficulty in opening or closing the device, or improper sealing of the mouthpiece, can result in reduced medication delivery or wastage.

Furthermore, many existing inhalers lack a convenient and hygienic way to shield the mouthpiece after use, which may discourage proper handling and storage. This can contribute to user error, inconsistent dosing, and reduced medication efficacy. Additionally, current solutions do not always provide an intuitive or user-friendly mechanism for opening and closing the inhaler or for maintaining the device's cleanliness between uses.

The need exists for an improved portable inhaler that addresses these limitations by providing a hygienic, protected, and easy-to-use device. Such an invention would help to enhance medication integrity, reduce contamination risk, and improve overall user experience and compliance.

SUMMARY OF THE INVENTION

The present invention provides an innovative approach to the above unresolved issues by incorporating a mouthpiece cover that opens to reveal the mouthpiece, which folds down for inhalation, then closes securely to enclose the mouthpiece within the body of the apparatus. This design signifies a meaningful advancement over current inhaler technology, promising increased safety, convenience, and effectiveness in respiratory medication delivery.

In one preferred embodiment, the apparatus comprises a body for holding the inhalant medicament or holding a container of the inhalant medicament, wherein the body also includes a nozzle for dispensing the inhalant medicament. The apparatus further comprises a hollow mouthpiece having an opening on either end, a first opening for receiving the inhalant medicament from the nozzle and a second opening for a user of the apparatus to receive the dispensed inhalant medicament, wherein the mouthpiece is connected to the body and configured to move between a mouthpiece closed position and a mouthpiece open position, wherein in the mouthpiece closed position the mouthpiece pivots, moves, or folds, upwards into the body, and wherein in the mouthpiece open position the mouthpiece pivots, moves, or folds, downwards from the body providing user access to the second opening of the mouthpiece. Another component of the first preferred embodiment is a cover connected to the body and configured to move between a cover closed position and a cover open position, wherein in the cover closed position the mouthpiece is in the mouthpiece closed position and the cover encloses the mouthpiece inside the body, and wherein in the cover open position the mouthpiece is in the mouthpiece open position and the user is provided access to the second opening of the mouthpiece. In aspects of this embodiment, the mouthpiece has at least one groove that operatively engages with at least one peg on the cover, such that as the user opens the cover into the cover open position, the mouthpiece is guided into the mouthpiece open position.

In a second preferred embodiment—in addition to the body, nozzle, mouthpiece, and cover noted above—the apparatus further includes a unique opening configuration, wherein the mouthpiece is forced into the mouthpiece open position using one or more torsion springs. To lock the springs and mouthpiece when the mouthpiece is in the closed position, protrusions on either or both sides of the mouthpiece are forced or otherwise moved in a backwardly direction along with part or all of the mouthpiece into or under one or more protrusions or openings within the body that hold, snap, or lock, the one or more mouthpiece protrusions in position, such that the one or more torsion springs are locked in place or unable to unwind or release when the mouthpiece is in the mouthpiece closed position. When opening the cover and mouthpiece, as the cover is opened, one or more pegs on the cover move through an open groove or cutout in the body such that the peg forces the one or more mouthpiece protrusions out of the one or more body protrusions or openings, thereby unlocking the one or more torsion springs and causing the one or more torsion springs to force the mouthpiece into the mouthpiece open position.

By using an apparatus as described herein, including the body, mouthpiece, and cover, the internal workings of the apparatus are protected, including the mouthpiece, when not in use, such as from damage, dirt, and contaminants.

BRIEF DESCRIPTION OF THE DRAWINGS

The accompanying drawings illustrate certain aspects and principles of the implementations set forth, and should not be construed as limiting.

FIG. 8 shows a bottom interior of the body, and the mouthpiece is transparent.

FIG. 9 shows a backside, bottom-half of the body. To the right is the cover in the cover open position (in dotted lines). Towards the front of the body and on the left of the figure is the mouthpiece in the mouthpiece open position (in dotted lines). This helps provide a close-up of the open groove or cutout in the body 11, as described in detail herein.

DETAILED DESCRIPTION OF THE INVENTION

Reference will now be made in detail to various illustrative implementations. It is to be understood that the following discussion of the implementations is not intended to be limiting.

First Preferred Embodiment

Figure 1:
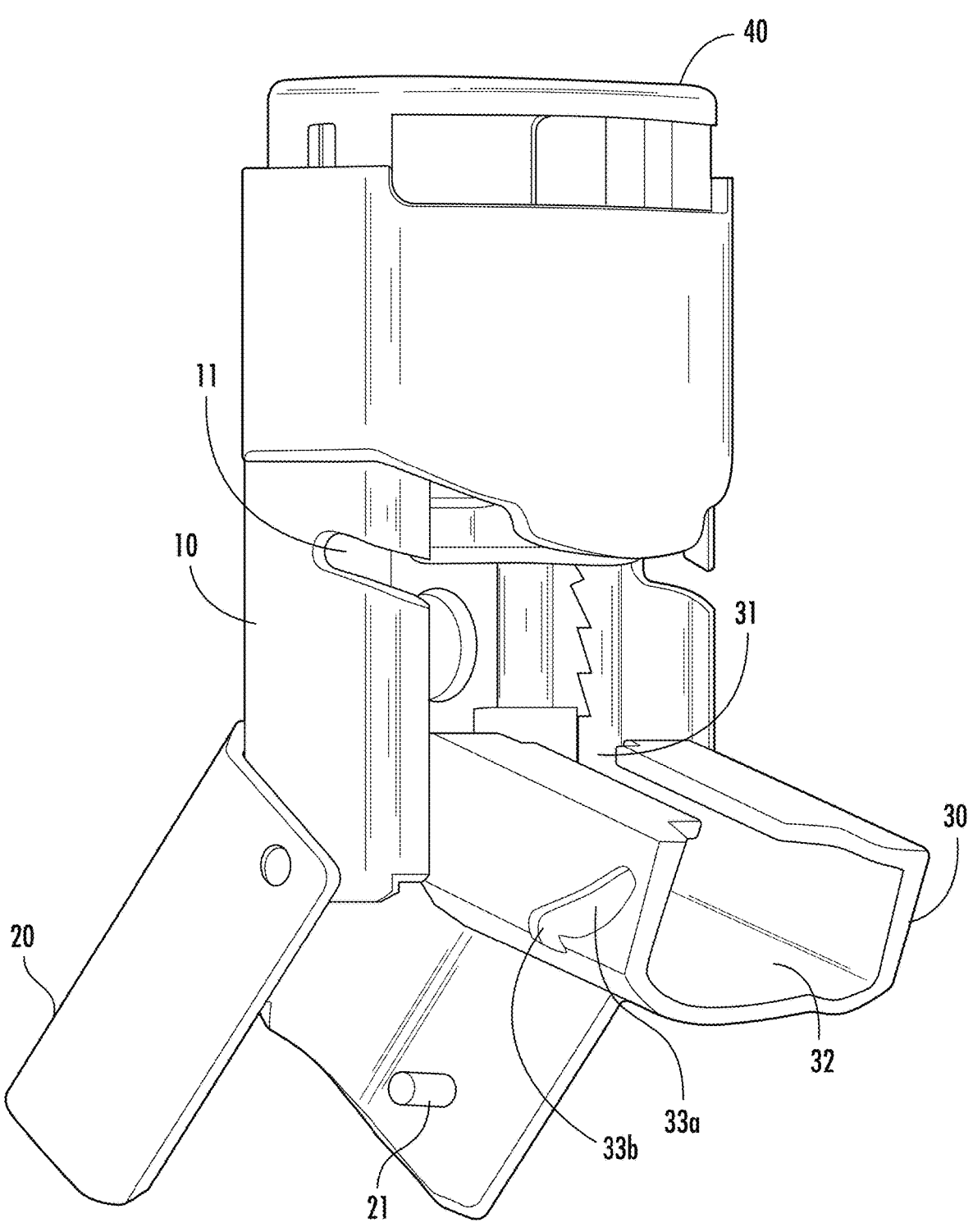
FIG. 1 is a depiction of a first preferred embodiment showing the apparatus in an open position, according to disclosures of the invention as described herein.

FIG. 1 depicts the first preferred embodiment of the invention in the open position. As depicted, the body 10 is connected to the cover 20 in a moveable manner so that it can be closed and opened, and moved between the open and closed position, such as swinging the cover up to close it, and swinging it down to open it. Also depicted is the mouthpiece 30 as revealed by the opened cover and in the open position as further described herein. As will be described in further detail, the mouthpiece can swing, pivot, move, flip, or fold, downwardly to open and upwardly to close. When in the closed position, the mouthpiece is enclosed in the body by the cover. As shown, the mouthpiece is hollow, so that one end 31 can receive dispensed medicament, and the other end 32 can be used by the user to inhale the dispensed medicament. Further depicted in FIG. 1 is a removably attachable top 40 that can be pressed down to dispense the medicament.

Figure 2:
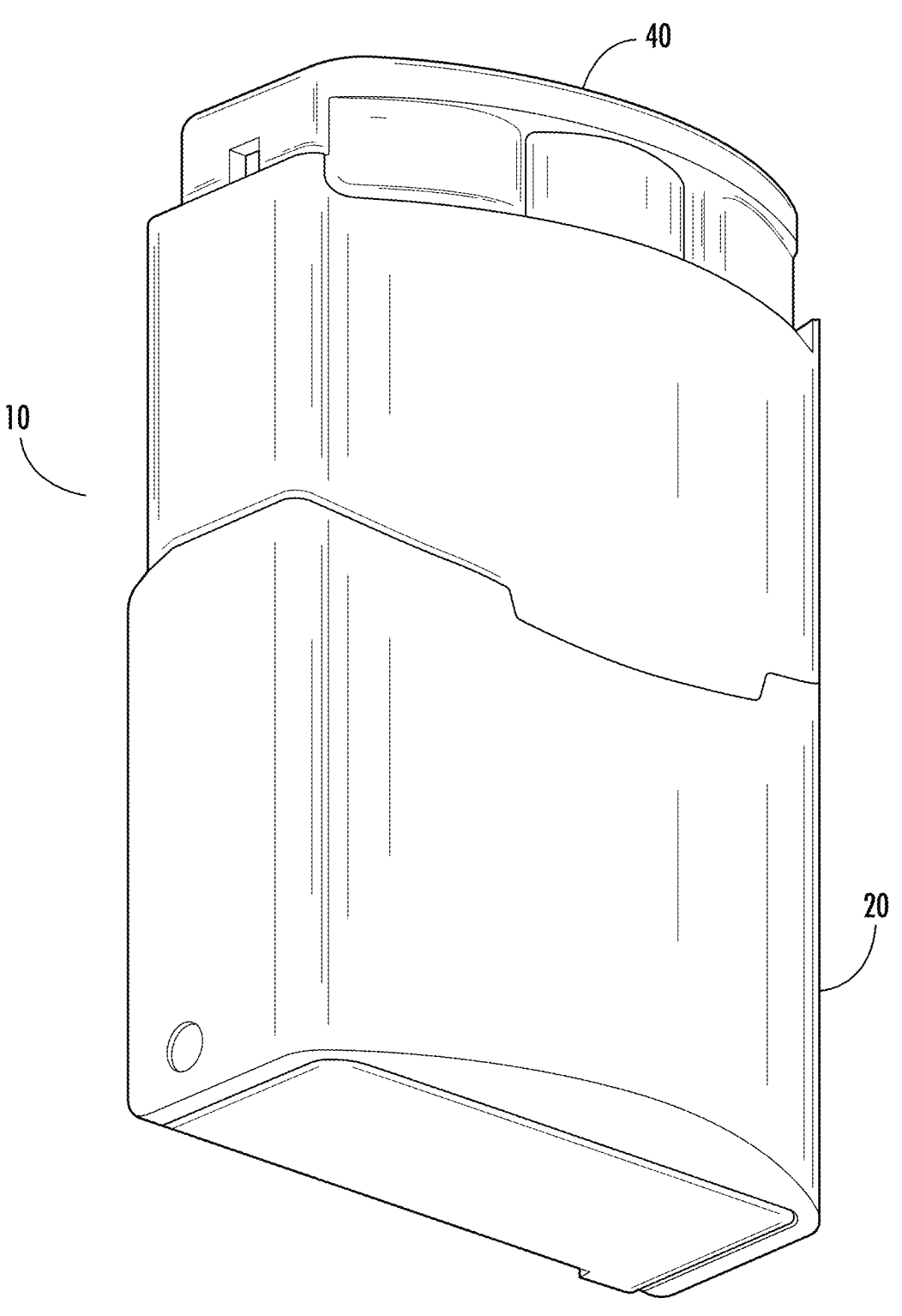
FIG. 2 is a depiction of a first preferred embodiment showing the apparatus in a closed position, according to disclosures of the invention as described herein.
Figure 3:
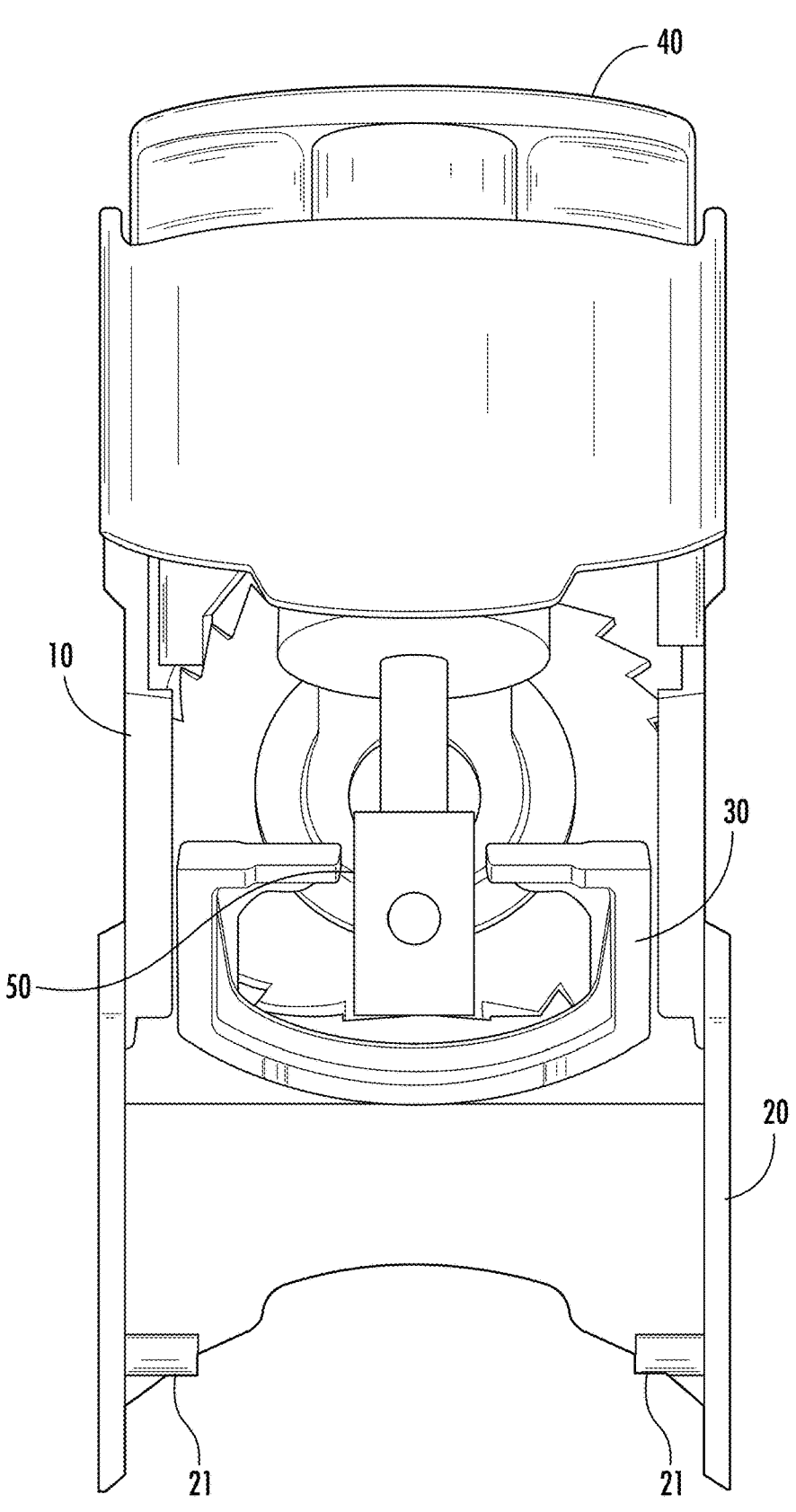
FIG. 3 is a depiction of a first preferred embodiment showing the apparatus in an open position and internal components of the apparatus exposed, according to disclosures of the invention as described herein.
Figure 4:
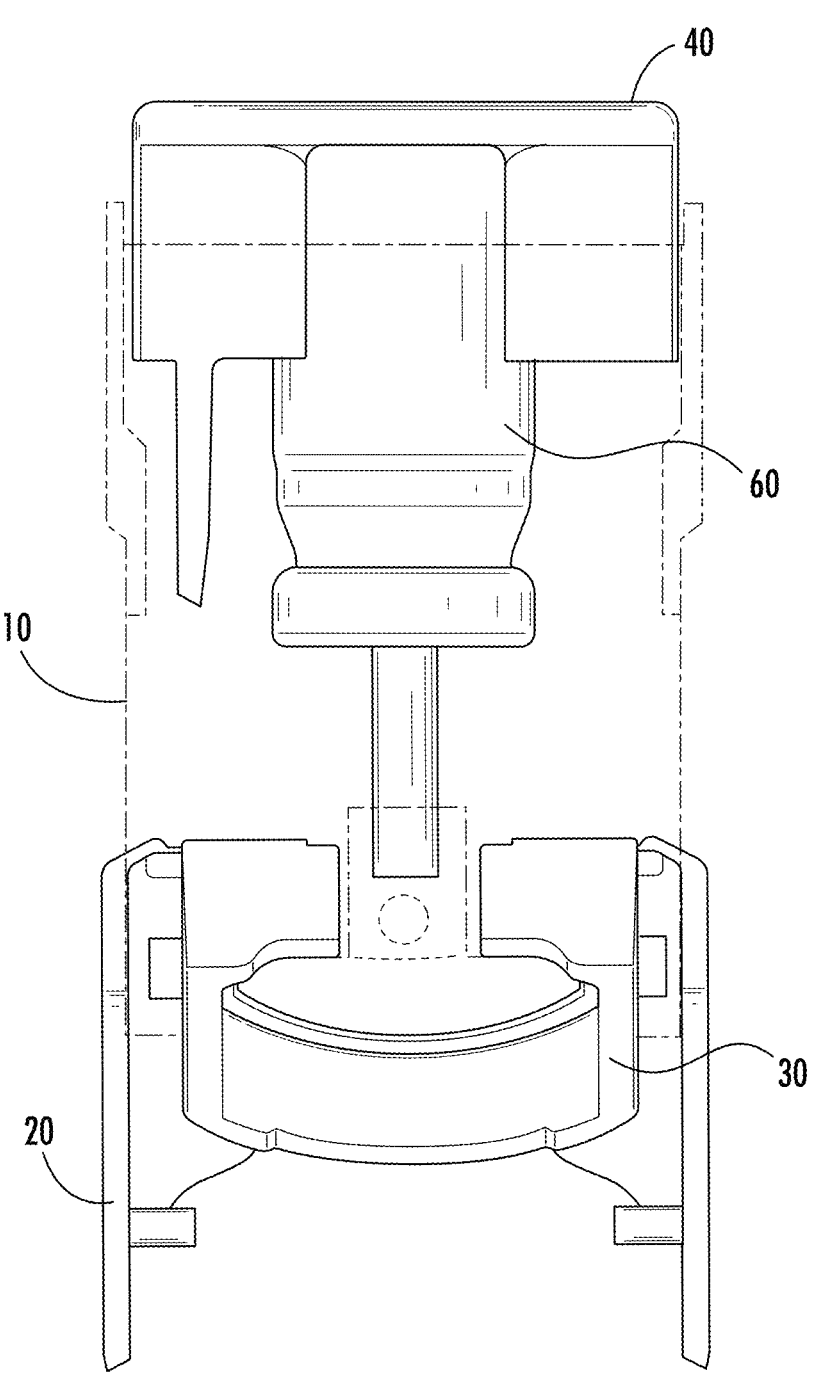
FIG. 4 is a depiction of a first preferred embodiment showing the apparatus in an open position and internal components of the apparatus exposed, according to disclosures of the invention as described herein.

FIG. 2 shows the first preferred embodiment in the closed position, wherein the cover 20 has been closed and the mouthpiece (not shown) is enclosed in the body 10, such as positioned substantially vertically within the body. FIG. 3 shows internal components of the apparatus, including a nozzle 50 for dispensing the inhalant medicament when the removably attachable top 40 is pressed down. In FIG. 3, also depicted in the open position is the body 10, the cover attached to the body 20, and the open mouthpiece 30. FIG. 4 depicts the first preferred embodiment in the open position, including a container 60 holding the inhalant medicament. In FIG. 4, also depicted in the open position is the body 10, the cover attached to the body 20, and the open mouthpiece 30. Please note that the body 10 is transparent in FIG. 4.

Figure 5:
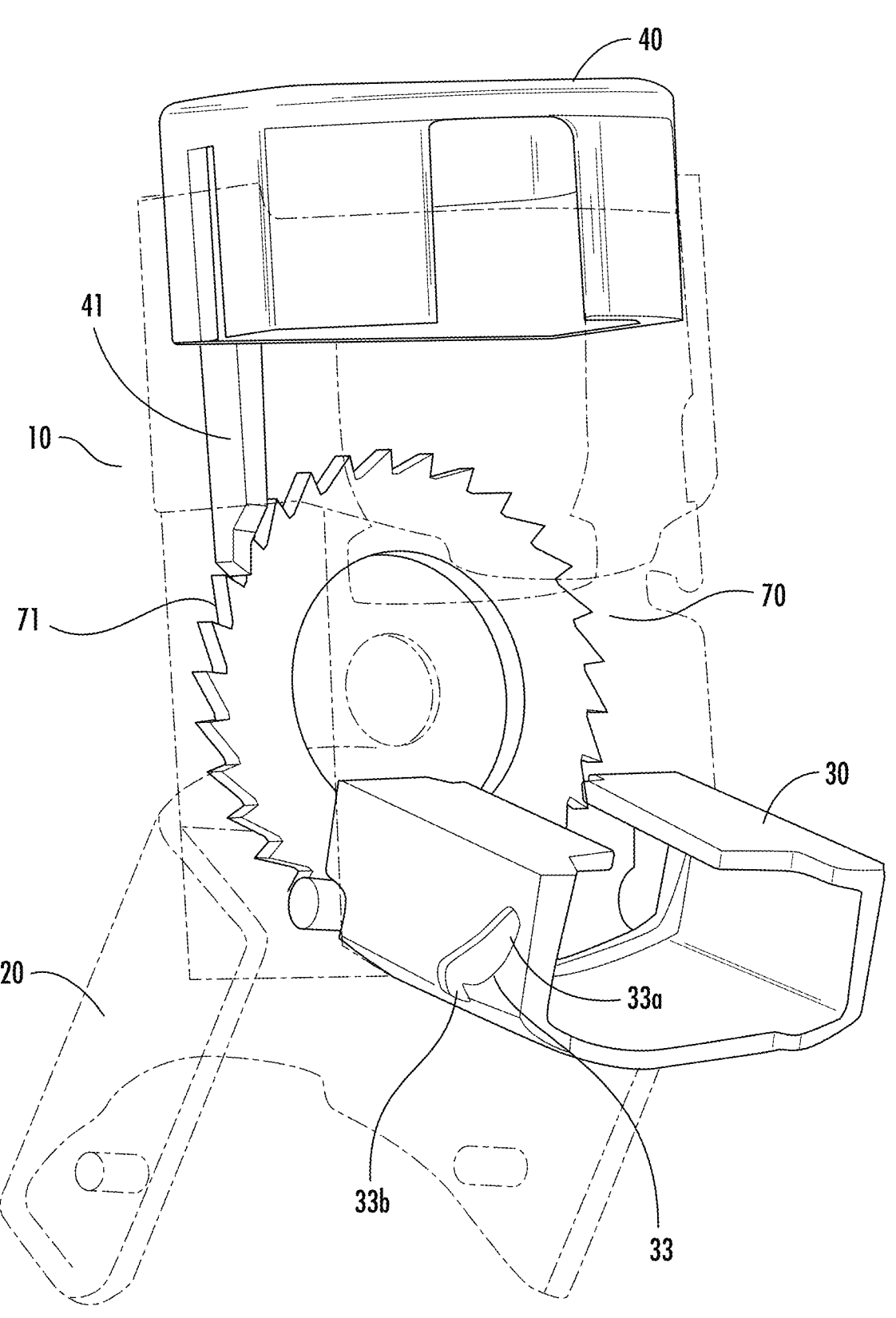
FIG. 5 is a depiction of a first preferred embodiment showing the apparatus in an open position and internal components of the apparatus exposed, according to disclosures of the invention as described herein.

According to the first preferred embodiment, the mouthpiece comprises at least one groove 33 (see, FIG. 1 and FIG. 5) that operatively engages with at least one peg 21 on the cover (see, FIG. 1, FIG. 3, and FIG. 4), such that as the user opens the cover into the cover open position, the mouthpiece is guided into the mouthpiece open position. In aspects, and as shown in FIG. 1 and FIG. 5, the at least one groove 33 can be curved or otherwise include an angle such that as the at least one peg 21 operatively engages with a first portion 33a of the groove, the at least one peg 21 forces the mouthpiece 30 to start moving into the mouthpiece open position, wherein a second portion 33b of the groove releases the at least one peg 21 from the at least one groove 33 such that the cover 20 is separated from the mouthpiece 30. In aspects, this design can have the one or more pegs apply, such as constantly apply, downward and/or diagonal force to unfold the mouthpiece until it reaches the mouthpiece open position, and not prematurely release the mouthpiece before it reaches its open position. When closing the cover 20, the at least one peg 21 operatively engages with the second portion 33b of the at least one groove 33 and moves into the first portion 33a of the at least one groove to force the mouthpiece 30 into the mouthpiece closed position. Moreover as shown in FIG. 1 and FIG. 5, by way of example, as the cover 20 is moved into the cover closed position, the at least one peg 21 operatively engaged with the at least one groove 33 forces the mouthpiece 30 to start moving into the mouthpiece closed position, and wherein as the cover 20 reaches the cover closed position, the mouthpiece 30 reaches the mouthpiece closed position, such that the mouthpiece is enclosed in the body 10 by the cover 20. In aspects, the at least one groove 33 is operatively engaged with the at least one peg 21 using a guide-and-mate or slide-in connection, providing for guided movement of the cover 20, the mouthpiece 30, or both. The closed position of the apparatus is shown in FIG. 2. In aspects, as shown in FIG. 1, the body comprises at least one cutout 11 to receive the at least one peg 21 when the cover 20 is in the cover closed position. In aspects, the mouthpiece when in the mouthpiece closed position or the cover when in the cover closed position, can prohibit dispensing of the inhalant medicament.

In aspects, and as depicted in, by way of example, FIG. 1, the cover can comprise two sides that completely or partially cover or overlap with two sides of the body when the cover is in the cover closed position (see FIG. 2). In aspects, the two sides of the cover and two sides of the housing body meet, and the two sides of the cover are held in the cover closed position against the two sides of the body using one or more of: a friction fit, a snap-lock, a snap-on fit, clamps or clips, a pressure fit, sealing mechanisms, gaskets, O-rings, a magnetic closure, a latch or locking mechanism, or an adhesive. Outwardly facing surfaces of those two sides of the cover can comprise: a texture, a Braille-like textured surface, a linear protrusion, a handle, a rounded protrusion, one or more nubs, a grooved pattern, ridges, treads, a knurled pattern, a raised pattern, a textured pattern, one or more dimples, one or more indentations, a textured coating, rubber, silicone, grit, one or more studs, one or more protuberances, a perforated pattern, or combinations thereof, such as to increase friction when, for example, the apparatus is being held or opened by a user.

As shown in FIG. 4, the body 10 (transparent in FIG. 4) can comprise a cavity for holding a container 60 (such as a cannister) of the inhalant medicament therein. In aspects, the container can be a pressurized cannister; the inhalant medicament can be aerosolized before inhalation by the user; the inhalant medicament can be in a dry powder form; the inhalant medicament can be provided to the user as a soft mist; or the inhalant medicament can be released when the user inhales the inhalant medicament. The apparatus can be a metered-dose inhaler, a dry powder inhaler, a soft mist inhaler, or a breath-actuated inhaler.

The apparatus can further include a removably attachable top 40, which, in aspects, can be removed or detached to connect the container 60 of the inhalant medicament to the removably attachable top 40, wherein once the container 60 of the inhalant medicament is connected to the removably attachable top 40, the removably attachable top 40 can be reattached to the body 10 such that the container 60 of the inhalant medicament is inserted into the body 10, as depicted in FIG. 4, and wherein the removably attachable top 40 can be operatively attached to the body 10 such that when the user pushes down on the removably attachable top 40, the inhalant medicament is dispensed through the nozzle and out the mouthpiece to the user. In this regard, pushing down on the removably attachable top compresses the container, such as a typical inhaler pressurized cannister, which would be understood by one of ordinary skill in the art, to dispense the inhalant medicament similar to a traditional inhaler; therefore, that functionality will remain familiar to the user.

In aspects, the removably attachable top and body can be configured such that the top is elevated over the top of the body, thereby causing a top portion of the surface of the container, such as a cannister, to be partially exposed. By way of example only, the removably attachable top can be attached to the container via a snap fit connection, or an adhesive.

In aspects, as shown in FIG. 5, the removably attachable top 40 can comprise a substantially vertical extension 41 that engages a ratchet-and-pawl system 70 in the body 10, such that pushing down on the removably attachable top 40 causes the substantially vertical extension 41 to engage one or more teeth 71 of the ratchet-and-pawl system 70 to move a dose counter number one position for each time the removably attachable top 40 is pressed down. In aspects, another extension in the body acting as a pawl 72 (see FIG. 8) also operatively engages with teeth 71 of the ratchet-and-pawl system 70, such as to hold it in place after it has been moved one dose counter number upon a user pushing down on the removably attachable top 40.

In aspects, the ratchet-and-pawl system can be located on the back wall of the body, and can comprise a saw tooth dose counting wheel. In aspects, a feature located above the ratchet-and-pawl system can hold the dose counting wheel in place, wherein the feature can be part of the body. The substantially vertical extension from the removably attachable top can fit in between the saw teeth on the dose counting wheel, and the body can contain a feature that serves as a pawl 72 for the saw teeth on the dose counting wheel. Although there is only one pawl featured in the figures, multiple pawls can be placed around the dose counting wheel to improve the dose counting mechanism.

In aspects, when the removably attachable top is pressed down to dispense the inhalant medicament, the container is compressed, and the substantially vertical extension on the removably attachable top is also moved downwardly, in some cases using a guide in the body. As maximum compression or substantially maximum compression is reached, the substantially vertical extension makes contact with one of the saw teeth on the counter wheel, rotating it until the next saw tooth gets locked in place by the pawl 72. In aspects, the pawl is flexible, allowing it to bend to improve accuracy and precision of the ratchet-and-pawl system. Moreover, the removably attachable top or the body can comprise a stop to restrict movement of the removably attachable top and the substantially vertical extension to rotating the counting wheel only one tooth. On a face of the counting wheel are numbers or other indicators, which, by way of example, can be displayed out of a window on the back of the body. When the apparatus is activated, the number displayed would decrease, and, as a result of the dose counter's saw tooth and pawl mechanism configuration, when the container is being uncompressed, such as by a spring-like characteristic of the metering valve, which, in aspects, is part of the internal mechanisms of the container, the number that is displayed would remain the same until the apparatus is activated again to dispense the inhalant medicament. In cases, once the dose counter displays the number zero, the next activation would return the number displayed back to the maximum number of doses. This allows for patients to swap out containers without having to replace other components.

Second Preferred Embodiment

Figure 6:
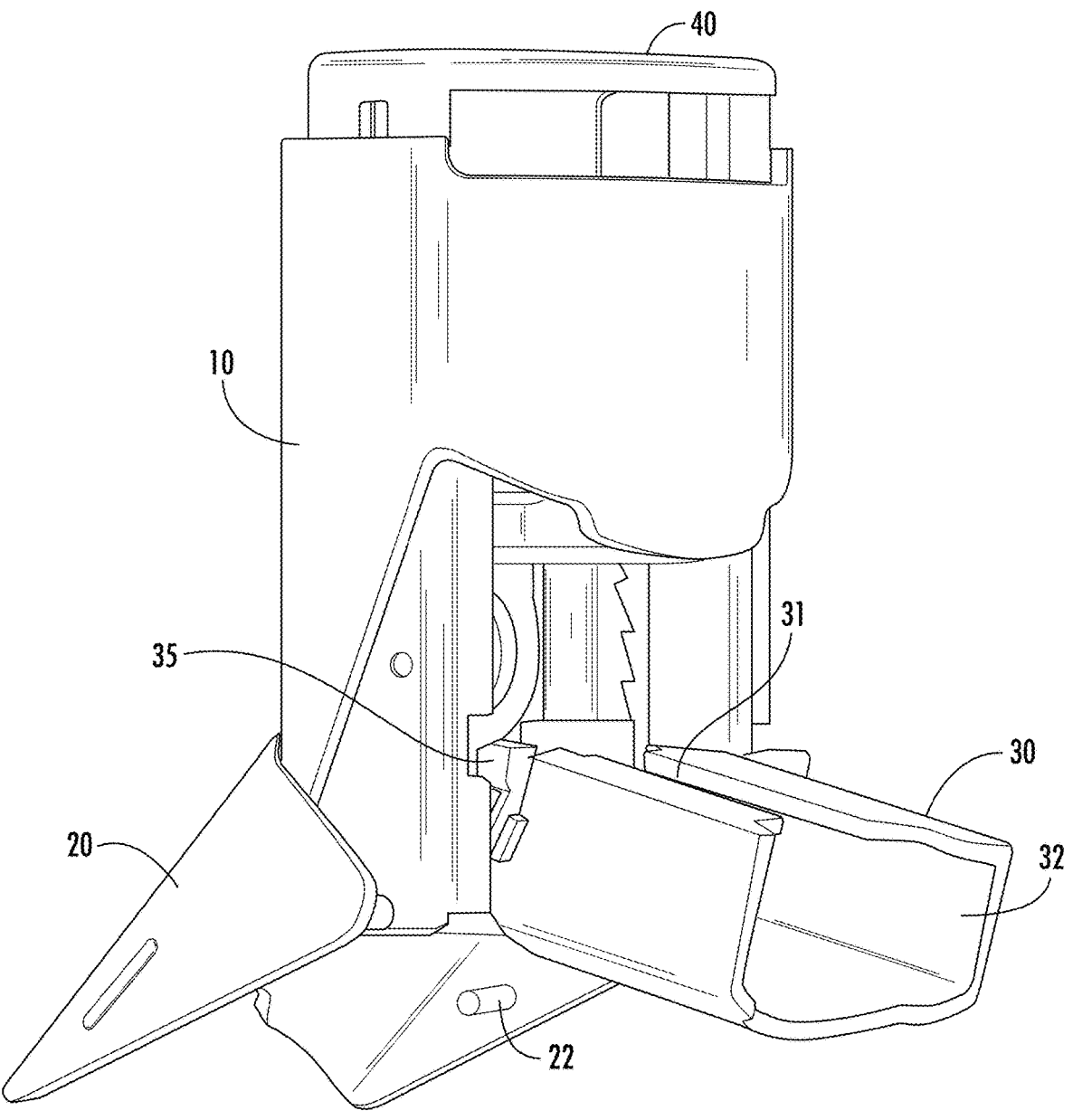
FIG. 6 is a depiction of a second preferred embodiment showing the apparatus in an open position and internal components of the apparatus exposed, according to disclosures of the invention as described herein.

In a second preferred embodiment, which shares many of the same elements of the first preferred embodiment—and therefore shared components between the two preferred embodiments will remain numbered consistently in all the figures—the mouthpiece is forced open using one or more torsion springs. FIG. 6 depicts the second preferred embodiment in the open position and including many of the same elements as the first preferred embodiment. For example, as shown in FIG. 6, the body 10 is connected to the cover 20 in a moveable manner so that it can be closed and opened, and moved between the open and closed position, such as swinging the cover up to close it, and swinging it down to open it. Also depicted is the mouthpiece 30 as revealed by the opened cover and in the open position as further described herein. The mouthpiece can swing, pivot, move, flip, or fold, downwardly to open and upwardly to close. When in the closed position, the mouthpiece is enclosed in the body by the cover, such as positioned substantially vertically within the body. As shown, the mouthpiece can be hollow, so that one end 31 can receive dispensed medicament, and the other end 32 can be used by the user to inhale the dispensed medicament. Further depicted in FIG. 1 is a removably attachable top 40 that can be pressed down to dispense the medicament. In the closed position, the second preferred embodiment will look similar or identical to the closed first preferred embodiment depicted in FIG. 2.

In the second preferred embodiment, the mouthpiece 30 can be forced into the mouthpiece open position using one or more torsion springs 80 (see FIG. 8, FIG. 10, FIG. 11, and FIG. 12, depicting the one or more torsion springs). The mouthpiece 30 can also include one or more mouthpiece protrusions 35 (see FIG. 6 and FIG. 7) on either or both sides of the mouthpiece 30, wherein as the mouthpiece 30 pivots, moves, or folds upwards into the body 10 and into the mouthpiece closed position, the one or more mouthpiece protrusions 35 (see FIG. 6 and FIG. 7) also pivot, move, or fold, in a backwardly direction into or under one or more body protrusions or openings 34 (see FIG. 8) within the body 10 that hold, snap, or lock, the one or more mouthpiece protrusions 35 in position, such that the one or more torsion springs 80 are locked in place or unable to unwind or release when the mouthpiece 30 is in the mouthpiece closed position. When moving the cover 20 into the cover open position, one or more pegs 22 (see FIG. 6) on the cover 20 move through an open groove or cutout 11 (see FIG. 8 and FIG. 9) in a bottom (or other) portion of the body 10 such that the one or more pegs 22 meet with and push or otherwise force the one or more mouthpiece protrusions 35 out of or under from the one or more body protrusions or openings 34, thereby unlocking the one or more torsion springs 80 and causing the one or more torsion springs 80 to force the mouthpiece 30 into the mouthpiece open position.

In aspects, the interior of the body can include one or more channels to accept and secure the one or more torsion springs 80. In aspects, there can also be one or more corresponding channels extending from or indented or recessed in each side of the mouthpiece, where the other side of the torsion spring(s) sit or otherwise contact so they can apply pressure/force to unfold the mouthpiece when the mouthpiece is unlocked and can be opened to the mouthpiece open position.

Other aspects and components of the second preferred embodiment are similar to the first preferred embodiment.

Figure 7:
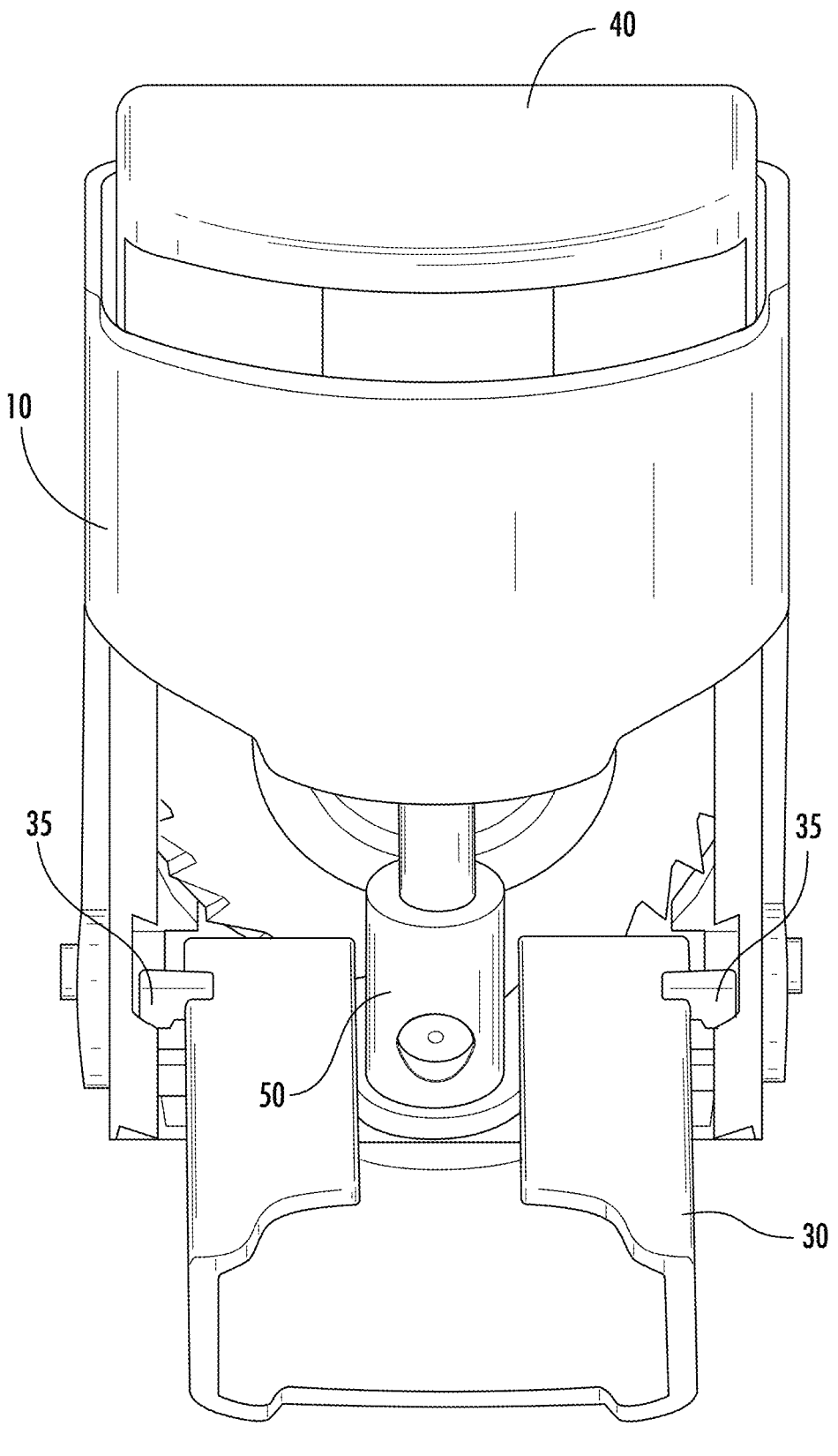
FIG. 7 is a depiction of a second preferred embodiment showing the apparatus in an open position and internal components of the apparatus exposed, according to disclosures of the invention as described herein.

For example, FIG. 6 and FIG. 7 show internal components of the apparatus, including a nozzle 50 for dispensing the inhalant medicament when the removably attachable top 40 is pressed down. In FIG. 6, also depicted in the open position, is the body 10, the cover attached to the body 20, and the open mouthpiece 30. While not depicted in the figures for the second preferred embodiment, the body can also hold a container holding the inhalant medicament as described in the first preferred embodiment. The container can be a pressurized cannister, the inhalant medicament can be aerosolized before inhalation by the user, the inhalant medicament can be in a dry powder form, the inhalant medicament can be provided to the user as a soft mist, the inhalant medicament can released when the user inhales the inhalant medicament, or combinations thereof. Similarly, in aspects, the mouthpiece when in the mouthpiece closed position or the cover when in the cover closed position, can prohibit dispensing of the inhalant medicament. In other words, when the mouthpiece is in the mouthpiece closed position, it can be configured to lock the container in place, and prevent it from being compressed until it is opened again. Like the first preferred embodiment, the second preferred embodiment can be a metered-dose inhaler, a dry powder inhaler, a soft mist inhaler, or a breath-actuated inhaler.

In aspects, and as depicted in, by way of example, FIG. 6, the cover can comprise two sides that completely or partially cover or overlap with two sides of the body when the cover is in the cover closed position. In aspects, the two sides of the cover and two sides of the housing body meet, and the two sides of the cover are held in the cover closed position against the two sides of the body using one or more of: a friction fit, a snap-lock, a snap-on fit, clamps or clips, a pressure fit, sealing mechanisms, gaskets, O-rings, a magnetic closure, a latch or locking mechanism, or an adhesive. Outwardly facing surfaces of those two sides of the cover can comprise: a texture, a Braille-like textured surface, a linear protrusion, a handle, a rounded protrusion, one or more nubs, a grooved pattern, ridges, treads, a knurled pattern, a raised pattern, a textured pattern, one or more dimples, one or more indentations, a textured coating, rubber, silicone, grit, one more studs, one or more protuberances, a perforated pattern, or combinations thereof, such as to increase friction when, for example, the apparatus is being held or opened by a user.

As shown in, for example, FIG. 6 and FIG. 7, the apparatus can further include a removably attachable top 40, which, in aspects, can be removed or detached to connect the container of the inhalant medicament (not depicted for the second preferred embodiment, but similar to the first preferred embodiment described above) to the removably attachable top 40, wherein once the container of the inhalant medicament is connected to the removably attachable top 40, the removably attachable top 40 can be reattached to the body 10 such that the container of the inhalant medicament is inserted into the body 10, and wherein the removably attachable top 40 can be operatively attached to the body 10 such that when the user pushes down on the removably attachable top 40, the inhalant medicament is dispensed through the nozzle and out the mouthpiece to the user. In aspects, as shown in, for example FIG. 4, and the same for both the first preferred embodiment and the second preferred embodiment, the nozzle 50 allows a valve stem to fit inside it through, for example, an opening on its top surface. Above the valve stem is the container, from which the valve post extends down from, in aspects. Inside the container 60, such as towards a bottom or bottom-necked end of the container, can be a metering valve, from which the valve stem can originate.

Similar to the first preferred embodiment and as described above, the second preferred embodiment can include the substantially vertical extension that engages a ratchet-and-pawl system in the body, such that pushing down on the removably attachable top causes the substantially vertical extension to engage one or more teeth of the ratchet-and-pawl system to move a dose counter number one position for each time the removably attachable top is pressed down. In aspects, another extension in the body (e.g., a pawl) also operatively engages with teeth of the ratchet-and-pawl system, such as to hold it in place after it has been moved one dose counter number upon a user pushing down on the removably attachable top. In aspects, the dose counter numbers can be seen on the back of the apparatus body.

Figure 8:
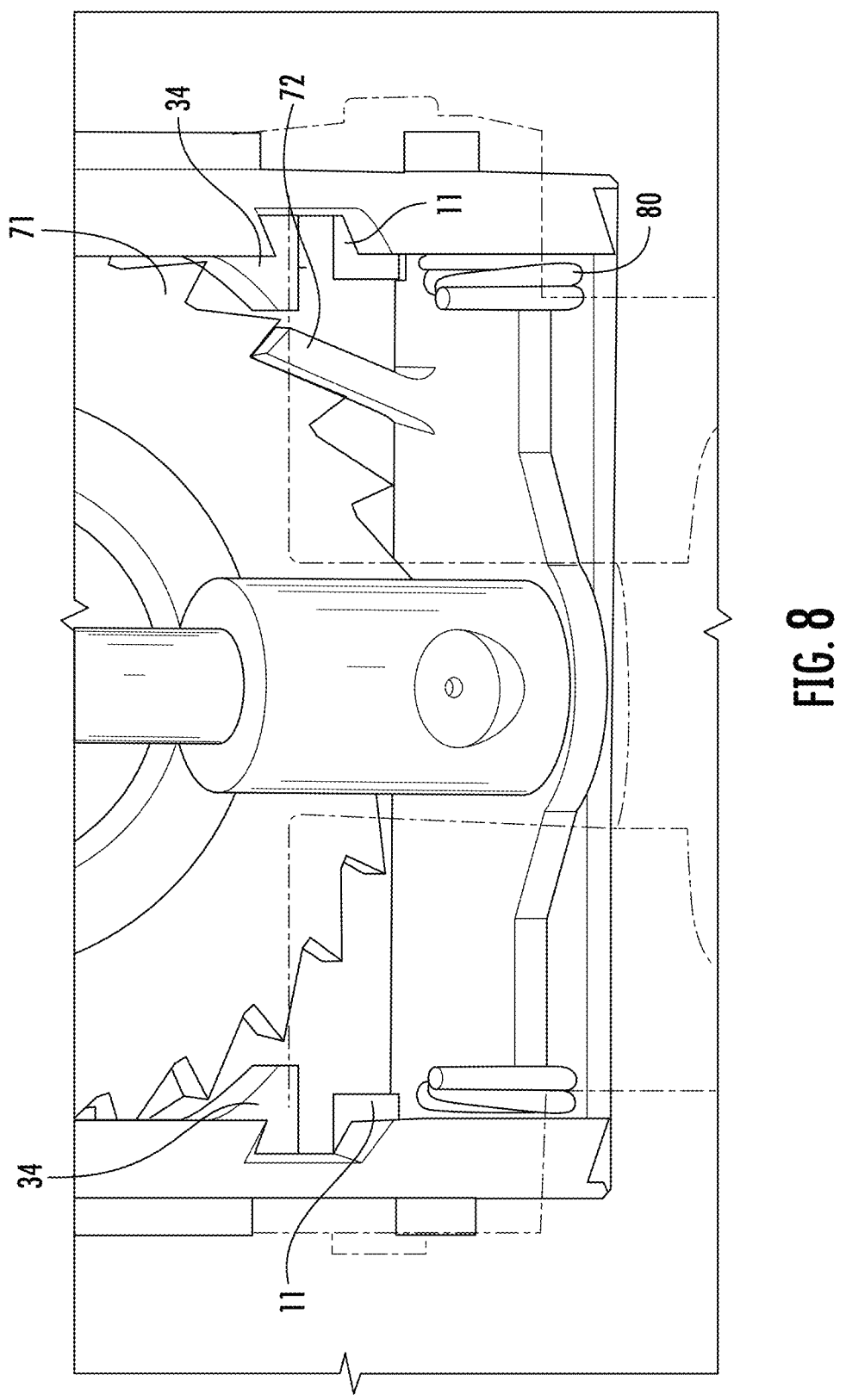
FIG. 8 is a depiction of a second preferred embodiment showing the apparatus in an open position and internal components of the apparatus exposed, including torsion springs, according to disclosures of the invention as described herein.
Figure 9:
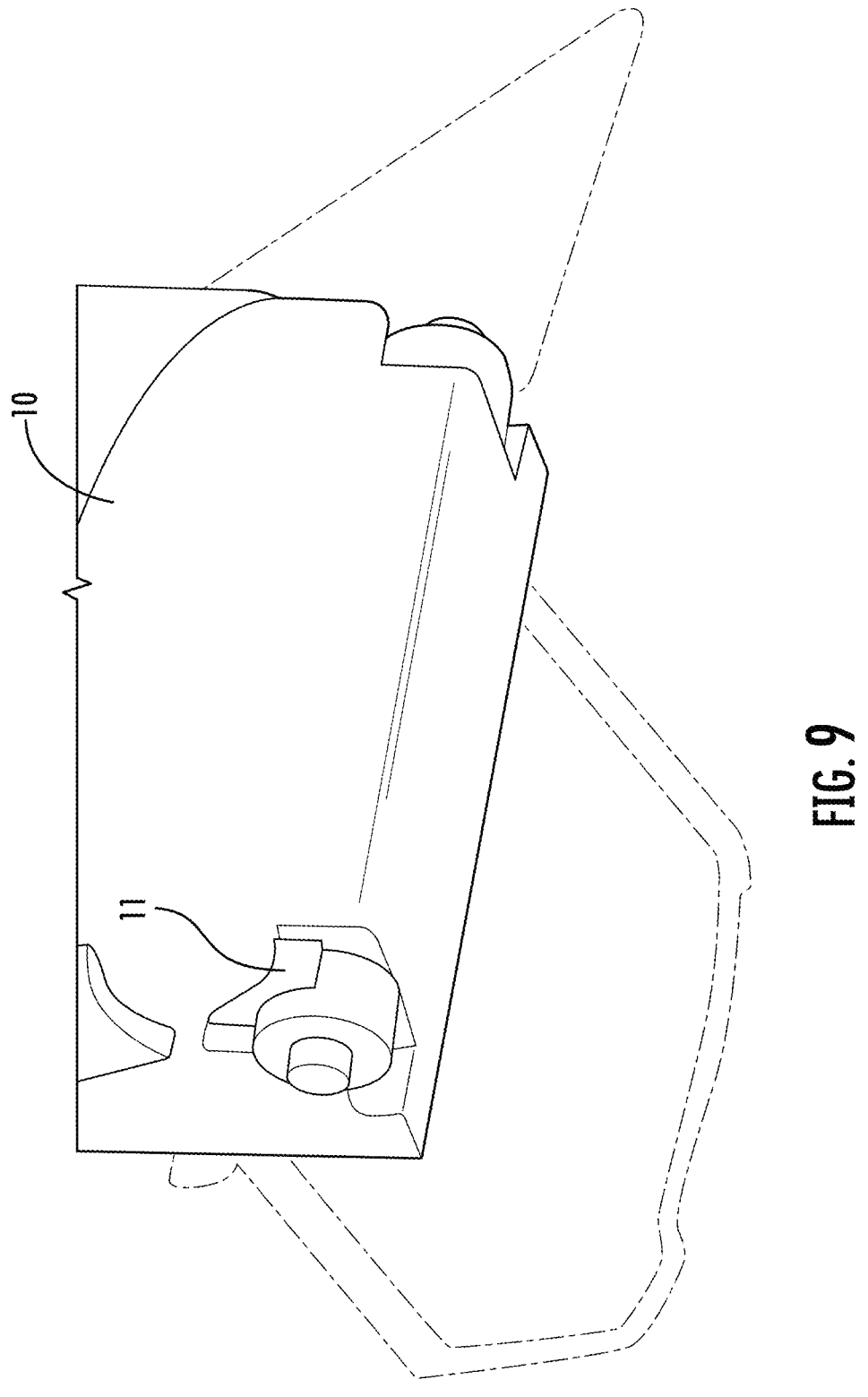
FIG. 9 is a depiction of a second preferred embodiment showing cutouts in the body for accepting pegs on the cover, according to disclosures of the invention as described herein.

Regarding FIG. 8 in more detail, it depicts the cutout 11 where the one or more pegs on the cover will force or kick out the mouthpiece protrusions when the cover is moved into the open position, thereby releasing the one or more torsion springs 80. Also depicted is the component 72 of the ratchet-and-pawl system that will stop the teethed gear after the removably attachable top is pushed down and the substantially vertical extension engages with the teeth and moves the gear one position. Also depicted are the protrusions or openings 34 in the body that will hold the mouthpiece protrusions in place (such as by friction), thereby locking the one or more torsion springs in place so they do not open the mouthpiece when in the closed position.

Figure 10:
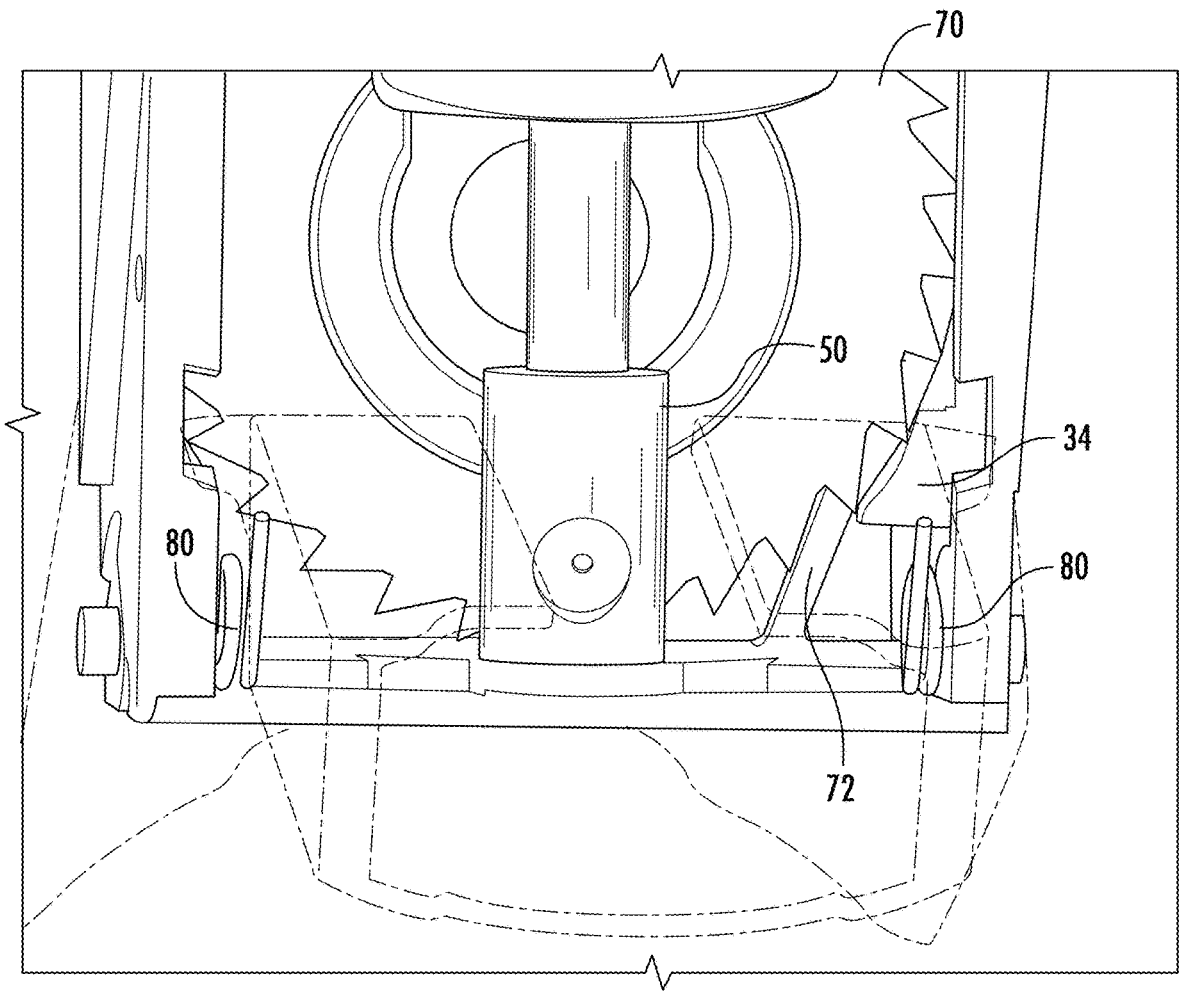
FIG. 10 is a depiction of a second preferred embodiment showing internal components of the apparatus exposed, according to disclosures of the invention as described herein.
Figure 11:
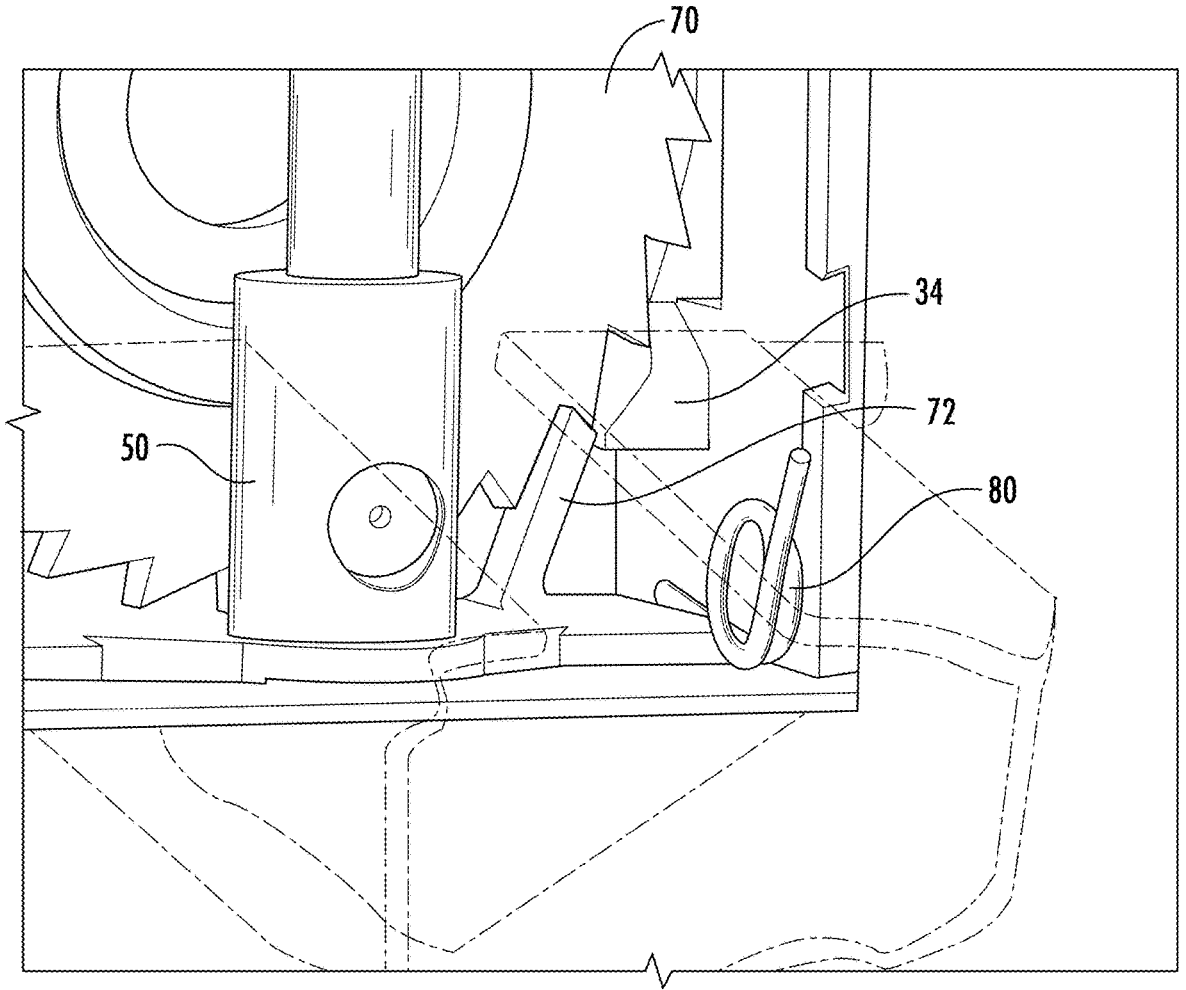
FIG. 11 is a depiction of a second preferred embodiment showing internal components of the apparatus exposed, according to disclosures of the invention as described herein.
Figure 12:
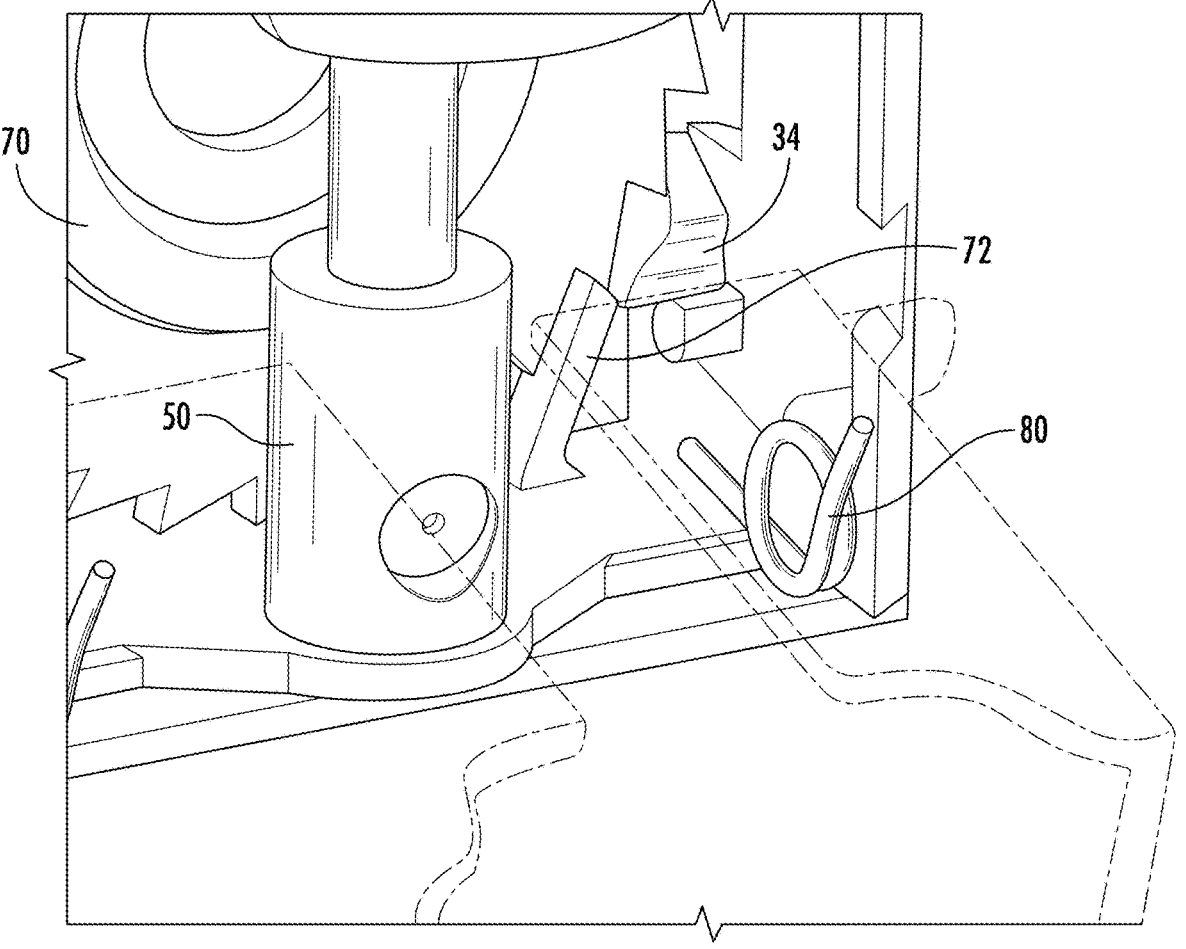
FIG. 12 is a depiction of a second preferred embodiment showing internal components of the apparatus exposed, according to disclosures of the invention as described herein.

FIG. 10, FIG. 11, and FIG. 12 further depict the one or more torsion springs 80. Also depicted is the component 72 of the ratchet-and-pawl system that will stop the teethed gear after the removably attachable top is pushed down and the substantially vertical extension engages with the teeth and moves the gear one position. Also depicted are the protrusions or openings 34 in the body that will hold the mouthpiece protrusions in place (such as by friction), thereby locking the one or more torsion springs in place so they do not open the mouthpiece when in the closed position. The nozzle 50 is shown, as well, and the ratchet-and-pawl system 70.

Cases for the Inhaler Apparatus

Figure 13:
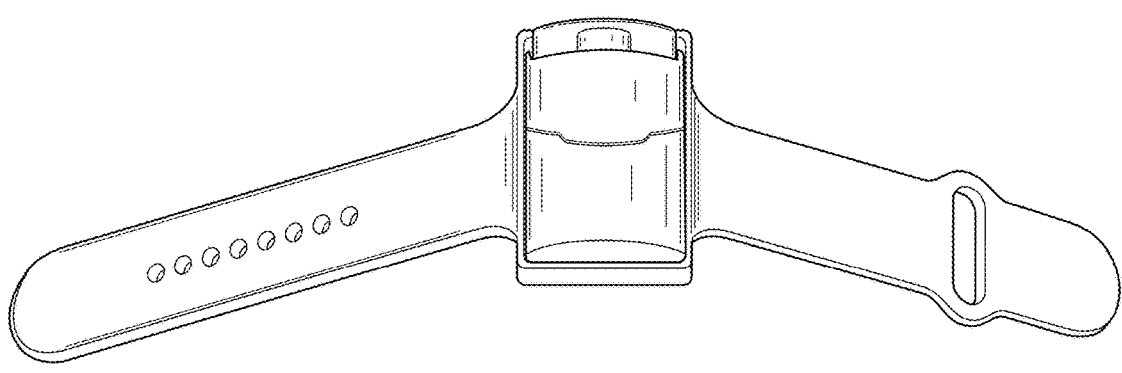
FIG. 13 includes depictions of inventive casings to hold and/or protect the embodiments of the inhaler apparatus, according to disclosures of the invention as described herein.
Figure 13:
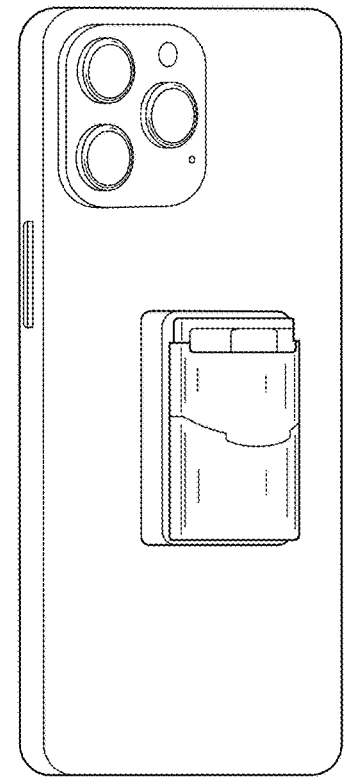
Figure 13:
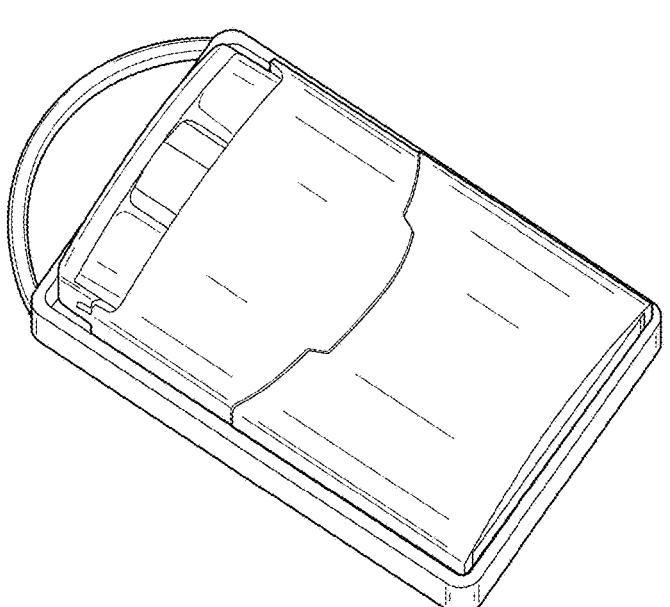

According to aspects of the present invention, the apparatus can be sized to attach to a back of a cellular phone, a keychain, and/or a wristband, as depicted in FIG. 13. For example, the present invention relates to a compact, portable inhaler apparatus designed to be conveniently integrated with electronic mobile devices, specifically mobile phones. Due to the configurations described herein, the inhaler can be engineered to be sufficiently small and lightweight, allowing it to be mounted on the back of a standard cell phone without adding significant bulk or weight. This integration facilitates easy accessibility for users, ensuring prompt relief during, for example, asthma episodes while on the go, such as exercising or traveling.

In an embodiment of the invention, the inhaler apparatus can be housed within or mounted onto a specially designed cell phone case. The case features a receptacle that is proportioned and shaped to securely receive and hold the inhaler in place. The receptacle may include a locking or friction-fit mechanism to maintain the inhaler's position and prevent accidental dislodgement. This arrangement not only protects the inhaler but also allows it to be readily accessible whenever the user needs it.

The design emphasizes portability, ease of use, and seamless integration with the user's daily routine, thereby promoting prompt and efficient management of medical symptoms. The invention aims to provide a practical, user-friendly solution for individuals requiring immediate access to an asthma inhaler in emergency or everyday situations.

Similarly, aspects of the current invention include a specially-designed wristband and a keychain holder, such that the inhaler apparatus can be housed within or mounted onto the wristband or keychain holder. Like the cell phone embodiment, the wristband and keychain feature a receptacle that is proportioned and shaped to securely receive and hold the inhaler in place. The receptacle may include a locking or friction-fit mechanism to maintain the inhaler's position and prevent accidental dislodgement.

In embodiments of the current invention, such as when sensors, controllers, or processors are used with the apparatus—such as with a "smart" inhaler—the apparatus may also include a computer readable medium comprising one or more computer files comprising a set of computer-executable instructions for performing one or more of the calculations, steps, processes, and operations. In exemplary embodiments, the computer readable medium has a set of instructions stored thereon which, when executed by a processor, cause the processor to perform tasks, based on data stored in the electronic database or memory described herein.

The computer or device performing the specified calculations, processes, steps, operations, algorithms, statistical methods, formulas, or computational routines may comprise at least one processing element such as a central processing unit (i.e., processor) and a form of computer-readable memory which may include random-access memory (RAM) or read-only memory (ROM).

Additional embodiments of this disclosure comprise a computer system for carrying out the computer-implemented method of this disclosure, such as for the "smart" inhaler. The computer system may comprise a processor for executing the computer-executable instructions, one or more electronic databases containing the data or information described herein, an input/output interface or user interface, and a set of instructions (e.g., software) for carrying out the method. The device may also interface with a network, which may use any suitable network protocol, including IP, UDP, or ICMP, and may be any suitable wired or wireless network including any local area network, wide area network, Internet network, telecommunications network, Wi-Fi enabled network, or Bluetooth enabled network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like.

For tracking and/or finding the apparatus when lost, the following can be integrated with the apparatus or used as part of the system:

GPS Module: The apparatus can include a GPS module to track the device's location, for example, in real time. This will allow users to pinpoint the apparatus's location via a connected app. Typically, users can access the device's location through an app on their smartphone or a web platform, giving them a precise map view of where the apparatus is located.

Bluetooth Proximity: Bluetooth technology can be used to identify when a user is in proximity to the apparatus. This is particularly useful for short-range tracking. An associated app on a user's smartphone can alert them if they are within a certain range of the apparatus, helping to locate it quickly in close quarters.

Wi-Fi Positioning: Known Wi-Fi networks can be used to assist in locating the apparatus more accurately indoors, where GPS might be weak. This method triangulates the apparatus's position based on nearby Wi-Fi signals and can be a helpful backup to GPS.

Sound Emitter: The apparatus can be equipped with a sound-emitting feature that can be activated, by way of example, remotely using an app or web platform. When users need to locate the apparatus within a building, for example, triggering an audible alert can guide them to its location, which can be especially useful amongst clutter or in low-light areas.

Light Emitter: An LED or other light source on the apparatus can be activated remotely to blink or light up, making it visible in dark environments. This is particularly helpful when the apparatus is lost in a dark room, under furniture, or during nighttime.

FID/NFC Tagging: RFID or NFC tags can be incorporated, which can be scanned by another device to confirm the apparatus's presence. Within close proximity, users with compatible reading devices can quickly verify the apparatus's location.

Combining these technologies can significantly enhance the apparatus's findability by providing multiple ways to detect and track its location, catering to different scenarios and environments.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purposes only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. An apparatus for dispensing an inhalant medicament comprising:
   a body for holding a container of the inhalant medicament;

a nozzle inside the body for dispensing the inhalant medicament;
   a hollow mouthpiece having an opening on either end, a first opening for receiving the inhalant medicament from the nozzle and a second opening for a user of the apparatus to receive the dispensed inhalant medicament, wherein the mouthpiece is connected to the body and configured to pivot, flip, or fold, between a mouthpiece closed position and a mouthpiece open position, wherein in the mouthpiece open position the mouthpiece is configured to pivot, flip, or fold, upwards into the body and to the mouthpiece closed position such that the second opening is facing in an upwardly direction, and wherein in the mouthpiece open closed position the mouthpiece is configured to pivot, flip, or fold, downwards from the body to the mouthpiece open position providing user access to the second opening of the mouthpiece; and
   a cover connected to the body configured to move between a cover closed position and a cover open position, wherein in the cover closed position the mouthpiece is in the mouthpiece closed position and the cover encloses the mouthpiece inside the body, and wherein in the cover open position the mouthpiece is in the mouthpiece open position and the user is provided access to the second opening of the mouthpiece; and wherein the mouthpiece comprises at least one groove that operatively engages with at least one peg on the cover, such that as the user opens the cover into the cover open position, the mouthpiece is guided into the mouthpiece open position.

2. The apparatus of claim 1, wherein as the cover is moved into the cover closed position, the at least one peg operatively engaged with the at least one groove forces the mouthpiece to start moving into the mouthpiece closed position, and wherein as the cover reaches the cover closed position, the mouthpiece reaches the mouthpiece closed position, such that the mouthpiece is enclosed in the body by the cover.

3. The apparatus of claim 1, wherein the at least one groove is operatively engaged with the at least one peg using a guide-and-mate or slide-in connection, providing for guided movement of the cover, the mouthpiece, or both.

4. The apparatus of claim 1, further comprising a cavity within the body for holding the container of the inhalant medicament therein, and wherein the container is a pressurized cannister, wherein the inhalant medicament is aerosolized before inhalation by the user, wherein the inhalant medicament is in a dry powder form, wherein the inhalant medicament is provided to the user as a soft mist, wherein the inhalant medicament is released when the user inhales the inhalant medicament, or combinations thereof.

5. The apparatus of claim 1, wherein the apparatus is a metered-dose inhaler, a dry powder inhaler, a soft mist inhaler, or a breath-actuated inhaler.

6. The apparatus of claim 1, further comprising a removably attachable top, which is removed or detached to connect the container of the inhalant medicament to the removably attachable top, wherein once the container of the inhalant medicament is connected to the removably attachable top, the removably attachable top is reattached to the body such that the container of the inhalant medicament is inserted into the body, and wherein the removably attachable top is operatively attached to the body such that when the user pushes down on the removably attachable top, the inhalant medicament is dispensed through the nozzle and out the mouthpiece second opening.

7. The apparatus of claim 6, wherein the removably attachable top comprises a substantially vertical extension that engages a ratchet-and-pawl system in the body, such that pushing down on the removably attachable top causes the substantially vertical extension to engage one or more teeth of the ratchet-and-pawl system to move a dose counter number one position for each time the removably attachable top is pressed down.

8. The apparatus of claim 1, wherein the mouthpiece when in the mouthpiece closed position or the cover when in the cover closed position, prohibit dispensing of the inhalant medicament.

9. The apparatus of claim 1, wherein the container of the inhalant medicament is part of the body itself, housed within the body, held within the body, located in a cavity of the body, embedded in the body, contiguous with the body, built-into the body, integrated with the body, seamless with the body, removable from the body, permanently in the body, fixed in the body, affixed to the body, secured to the body, fastened to the body, attached to the body, connected to the body, inseparable from the body, or manufactured or fabricated as part of the body; or wherein a part or a portion inside the body serves as the container of the inhalant medicament, wherein the container of the inhalant medicament is incorporated as a part or a portion of the body, or wherein all or part of the body act as the container of the inhalant medicament.

10. The apparatus of claim 1, wherein the cover comprises two sides that completely or partially cover or overlap with two sides of the body when the cover is in the cover closed position, such that the two sides of the cover and the two sides of the housing body meet, and the two sides of the cover are held in the cover closed position against the two sides of the body using one or more of: a friction fit, a snap-lock, a snap-on fit, clamps or clips, a pressure fit, sealing mechanisms, gaskets, O-rings, a magnetic closure, a latch or locking mechanism, or an adhesive.

11. The apparatus of claim 10, wherein one or more outwardly facing surfaces of the two sides of the cover comprise: a texture, a braille-like textured surface, a linear protrusion, a handle, a rounded protrusion, one or more nubs, a grooved pattern, ridges, treads, a knurled pattern, a raised pattern, a textured pattern, one or more dimples, one or more indentations, a textured coating, rubber, silicone, grit, one more studs, one or more protuberances, a perforated pattern, or combinations thereof.

12. The apparatus of claim 1, wherein the apparatus is sized to attach to a back of a cellular phone, a keychain, and/or a wristband.

13. The apparatus of claim 1, wherein the inhalant medicament is selected from the group consisting of: albuterol, levalbuterol, salbutamol, salmeterol, formoterol, budesonide, fluticasone propionate, fluticasone furoate, mometasone, beclomethasone, ciclesonide, ipratropium bromide, tiotropium, aclidinium, umeclidinium, glycopyrrolate, vilanterol, olodaterol, indacaterol, epinephrine, cromolyn sodium, omalizumab, nedocromil, montelukast, nicotine, naloxone, ketamine, loxapine, tobramycin, colistimethate sodium, amikacin, insulin, glucagon, glucagon-like peptide-1, tirzepatide, semaglutide, treprostinil, iloprost, antibiotics, antifungals, antipsychotics, corticosteroids, bronchodilators, mucolytics, or any combination thereof, including any investigational, experimental, or approved respiratory, psychotropic, metabolic, anti-infective, or emergency therapeutic agents deliverable via inhalation.

14. An apparatus for dispensing an inhalant medicament comprising:

a body for holding a container of the inhalant medicament;

a nozzle inside the body for dispensing the inhalant medicament;

a hollow mouthpiece having an opening on either end, a first opening for receiving the inhalant medicament from the nozzle and a second opening for a user of the apparatus to receive the dispensed inhalant medicament, wherein the mouthpiece is connected to the body and configured to move between a mouthpiece closed position and a mouthpiece open position, wherein in the mouthpiece open position the mouthpiece is configured to pivot, move, or fold, upwards into the body and to the mouthpiece closed position, and wherein in the mouthpiece closed position the mouthpiece is configured to pivot, move, or fold, downwards from the body to the mouthpiece open position providing user access to the second opening of the mouthpiece; and a cover connected to the body configured to move between a cover closed position and a cover open position, wherein in the cover closed position the mouthpiece is in the mouthpiece closed position and the cover encloses the mouthpiece inside the body, and wherein in the cover open position the mouthpiece is in the mouthpiece open position and the user is provided access to the second opening of the mouthpiece;

wherein the mouthpiece comprises at least one groove that operatively engages with at least one peg on the cover, such that as the user opens the cover into the cover open position, the mouthpiece is guided into the mouthpiece open position; and wherein the at least one groove is curved such that as the at least one peg operatively engages with a first portion of the groove, the at least one peg forces the mouthpiece to start moving into the mouthpiece open position, wherein a second portion of the groove releases the at least one peg from the at least one groove such that the cover is separated from the mouthpiece, and wherein when closing the cover, the at least one peg operatively engages with the second portion of the at least one groove and moves into the first portion of the at least one groove to force the mouthpiece into the mouthpiece closed position.

15. An apparatus for dispensing an inhalant medicament comprising:

a body for holding a container of the inhalant medicament;

a nozzle inside the body for dispensing the inhalant medicament;

a hollow mouthpiece having an opening on either end, a first opening for receiving the inhalant medicament from the nozzle and a second opening for a user of the apparatus to receive the dispensed inhalant medicament, wherein the mouthpiece is connected to the body and configured to move between a mouthpiece closed position and a mouthpiece open position, wherein in the mouthpiece open position the mouthpiece is configured to pivot, move, or fold, upwards into the body and to the mouthpiece closed position, and wherein in the mouthpiece closed position the mouthpiece is configured to pivot, move, or fold, downwards from the body to the mouthpiece open position providing user access to the second opening of the mouthpiece; and a cover connected to the body configured to move between a cover closed position and a cover open position, wherein in the cover closed position the mouthpiece is in the mouthpiece closed position and the cover encloses the mouthpiece inside the body, and wherein in the cover open position the mouthpiece is in the mouthpiece open position and the user is provided access to the second opening of the mouthpiece;

wherein the mouthpiece comprises at least one groove that operatively engages with at least one peg on the cover, such that as the user opens the cover into the cover open position, the mouthpiece is guided into the mouthpiece open position; and wherein the body comprises at least one cutout to receive the at least one peg when the cover is in the cover closed position.

16. An apparatus for dispensing an inhalant medicament comprising:

a body for holding a container of the inhalant medicament;

a nozzle inside the body for dispensing the inhalant medicament;

a hollow mouthpiece having an opening on either end, a first opening for receiving the inhalant medicament from the nozzle and a second opening for a user of the apparatus to receive the dispensed inhalant medicament, wherein the mouthpiece is connected to the body and configured to move between a mouthpiece closed position and a mouthpiece open position, wherein in the mouthpiece open position the mouthpiece is configured to pivot, move, or fold, upwards into the body and to the mouthpiece closed position, and wherein in the mouthpiece closed position the mouthpiece is configured to pivot, move, or fold, downwards from the body to the mouthpiece open position providing user access to the second opening of the mouthpiece; and a cover connected to the body configured to move between a cover closed position and a cover open position, wherein in the cover closed position the mouthpiece is in the mouthpiece closed position and the cover encloses the mouthpiece inside the body, and wherein in the cover open position the mouthpiece is in the mouthpiece open position and the user is provided access to the second opening of the mouthpiece;

wherein the mouthpiece is forced into the mouthpiece open position using one or more torsion springs; and wherein the mouthpiece further comprises one or more mouthpiece protrusions on either or both sides of the mouthpiece, wherein as the mouthpiece pivots, moves, or folds upwards into the body and into the mouthpiece closed position, the one or more mouthpiece protrusions pivot, move, or fold in a backwardly direction into or under one or more body protrusions or openings within the body that hold, snap, or lock, the one or more mouthpiece protrusions in position, such that the one or more torsion springs are locked in place or unable to unwind or release when the mouthpiece is in the mouthpiece closed position, wherein moving the cover into the cover open position moves one or more pegs on the cover through an open groove or cutout in the body such that the peg forces the one or more mouthpiece protrusions out of or under from the one or more body protrusions or openings, thereby unlocking the one or more torsion springs and causing the one or more torsion springs to force the mouthpiece into the mouthpiece open position.

* * * * *